United States Patent [19]
Sussman

[11] Patent Number: 6,062,856
[45] Date of Patent: May 16, 2000

[54] DENTAL IMPLANT HOLE GUIDE EXTENSION

[76] Inventor: Harold I. Sussman, 64 Popham Rd., Scarsdale, N.Y. 10583

[21] Appl. No.: 09/305,565
[22] Filed: May 5, 1999
[51] Int. Cl.⁷ ....................................................... A61C 3/02
[52] U.S. Cl. ................................................................ 433/76
[58] Field of Search ................................. 433/76, 72, 75; 33/513, 514

[56] References Cited

U.S. PATENT DOCUMENTS

| | | | |
|---|---|---|---|
| 5,741,133 | 4/1998 | Gordils et al. | 433/76 |
| 5,842,859 | 12/1998 | Palacci | 433/72 |
| 5,888,065 | 3/1999 | Sussman | 433/76 |

*Primary Examiner*—John J. Wilson
*Assistant Examiner*—Melba Bumgarner
*Attorney, Agent, or Firm*—Notaro & Michalos P.C.

[57] ABSTRACT

A dental implant hole guide extension is for use with or without an arrangement for drilling an initial hole, the arrangement having tooth engagement jaws for engaging a tooth which is adjacent a site in a patient's mouth for receiving the initial hole, a fixing mechanism connected to the jaws for fixing the jaws to the tooth and a guide member connected to the jaws and adapted to extend over the initial hole, the guide member having a first guide aligned with the initial hole. The extension includes a positioning pin for engagement in the first guide, an arm connected to the pin, a guide member engaging fork connected to the arm on one side of the pin for firmly engaging the guide member to hold the arm to the guide member or to rest at two points on the jaw bone crest if the extension is used without the guide, and a second guide connected to the arm on an opposite side of the pin for guiding a dental bur for drilling the subsequent implant hole.

24 Claims, 5 Drawing Sheets

DENTAL IMPLANT HOLE GUIDE EXTENSION

FIELD AND BACKGROUND OF THE INVENTION

The present invention relates in general to dental implants, and in particular to a new and useful dental implant hole guide extension which provides a dentist with an accurate guide to follow for drilling a second and subsequent holes after the critical initial pilot hole for dental implants so that the subsequent holes are aligned on an acceptable axis in the patient's jaw bone, without endangering adjacent teeth.

The present invention is for use with a dental implant hole guide arrangement disclosed in U.S. Pat. No. 5,888,065 issued Mar. 30, 1999 to the inventor of the present application and incorporated here by reference. The dental implant hole guide arrangement of U.S. Pat. No. 5,888,065 allows a dentist to make the critical first hole for an implant without endangering adjacent teeth.

Since 1981, dental root form implants have become a standard procedure for replacing missing teeth. Unlike other dental procedures such as crown and bridge work, root canals and the like, which utilize at least part of the original tooth as a foundation for the tooth replacement, implants require the drilling of holes directly into the bone of the jaw.

Although the dental implants have many benefits, particularly where a patient is missing teeth over large portions of the mouth, various complications can follow implant placement, especially to adjacent teeth. The bone may be overheated during implant surgery for example and this can devitalize an adjacent tooth. Endodontic lesions can also form which compromise the implant fixture by preventing integration of the bone around the fixture (Osseointegration) causing loss of the implant.

Another potentially more serious problem involves traumatic injury to the root of an adjacent tooth which is in the path of the hole drilled for the implant.

The case history of such a traumatic injury can be found in the inventor's article "Tooth Devitalization Via Implant Placement: A Case Report", Sussman, *Periodontal Clinical Investigations*, Vol. 20, No. 1, 1998, Northeastern Society of Periodontics, pp. 22–24.

U.S. Pat. No. 5,888,065 solves this problem by providing a dental implant hole guide arrangement for use in drilling a pilot hole for a dental implant which has an acceptable axis, the arrangement comprising tooth engagement means for engaging a tooth which is near the site in the patient's mouth for receiving the pilot hole, a fixing mechanism for fixing the engagement means to the tooth so that it does not move readily, and a guide member connected to the tooth engagement means and extending over the site, the guide member having a guide which is aligned with the acceptable axis of the pilot hole and which can be used to guide the movement of a dental bur for drilling the pilot hole.

Another more complex and time consuming technique for properly aligning the initial implant hole for a patient is disclosed in U.S. Pat. No. 5,015,183 entitled LOCATING DEVICE AND METHOD OF PLACING A TOOTH IMPLANT. According to this method, a stent comprising a negative impression of a patient's teeth in the vicinity of the implant is taken. Multiple x-ray opaque strips are placed in the negative impression and an oblique x-ray is taken. This x-ray is used as a diagnostic tool for the patient's jaw structure to help plot the trajectory of an implant fixture in the jaw.

Once an acceptable initial implant hole is formed in the jaw, subsequent holes can be produced by using the initial hole as a guide. This is when multiple implants are to be installed. See, for example, U.S. Pat. Nos. 5,741,133 and 5,302,122. Other techniques and apparatuses for drilling holes in the jaw bone are disclosed in U.S. Pat. Nos. 4,787,848 and 4,998,881. A need remains, however, for a simple and effective tool which can be used particularly by general dentists to permit them to produce the initial pilot hole along an acceptable axis in a patient's jaw bone. Once the initial bore is made, it can be enlarged to the required final diameter, generally about 4 mm., using ever increasing bur sizes. Once the initial hole is drilled, the enlargements are easily made using the initial hole as the guide. The present invention provides a way of making that critical initial hole.

Fixture positioning guides for guiding a dental drill to make a subsequent implant hole at fixed spacing from a previous one are available from Nobel Biocare AB under the trademark BRANEMARK SYSTEM. The guides include a post which is inserted into the previous hole. A guide block extends laterally of the first hole and a drill can be guided along a concave surface at the end of the block to form the subsequent hole. There is no mechanism in the BRANEMARK SYSTEM for fixing the center on the hole in the buccal/lingual direction however, because the block can rotate freely with the post in the first hole.

SUMMARY OF THE INVENTION

The present invention is used to drill a subsequent properly aligned implant hole after the first properly aligned pilot or finished implant hole has been formed. It is conventional to drill an initial small diameter hole, about 2 mm, followed by enlarging the hole until the appropriate size for the implant is reached. This is done using different burs of ever increasing diameter until a final hole diameter of about 4 mm is reached.

According to the present invention, the device of U.S. Pat. No. 5,888,065 is first used to create the first hole. The device has a guide to align the first pilot hole. The present invention is an extension for the guide for making the subsequent pilot or finished implant holes.

Accordingly, an object of the present invention is to provide an extension for a dental implant hole guide arrangement having tooth engagement means for engaging a tooth near a site in the patient's mouth for receiving an initial hole, a fixing mechanism for fixing the engagement means to the tooth so that it does not move readily, and a guide member connected to the tooth engagement means and extending over the site, the guide member having a first guide which is aligned with an acceptable axis of the initial hole and which can be used to guide the movement of a dental bur for drilling the initial hole. The extension comprises a positioning pin for engagement in the first guide and in the initial hole, an arm connected to the pin, guide member engaging means connected to the arm on one side of the pin for firmly engaging the guide member to hold the arm to the guide member and a second guide connected to the arm on an opposite side of the pin for guiding a dental bur for drilling the subsequent implant hole.

A still further object of the present invention is to provide a dental implant hole guide extension which can be used without the arrangement for drilling the initial hole but which, by itself, provides a 3 point contact with the patient's jaw. The extension of the present invention can be used both to guide drilling of the second implant hole and also as a measuring gauge for the proper alignment and depth of the initial hole.

Advantages of the invention include simplicity of construction with the preferred embodiment having only one part which is sterilizeable.

The guide extension of the present invention provides three-point contact with the guide arrangement to insure that the second guide is orthogonal to the jaw bone and parallel to the adjacent tooth. This properly aligns a guide trough or hole of the second guide, giving the dentist a clear guide to follow for drilling the subsequent hole.

The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which a preferred embodiment of the invention is illustrated.

DESCRIPTION OF THE PREFERRED EMBODIMENTS

Figure 1:
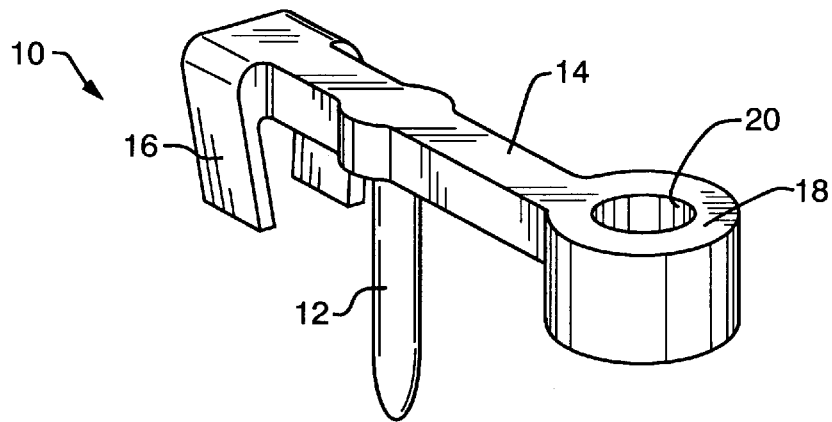
FIG. 1 is a perspective view of a dental implant hole guide extension of the present invention.

Referring to the drawings, the invention embodied therein is a new dental guide extension for guiding the formation of a subsequent hole after an initial pilot or finished implant hole has been formed.

Figure 2:
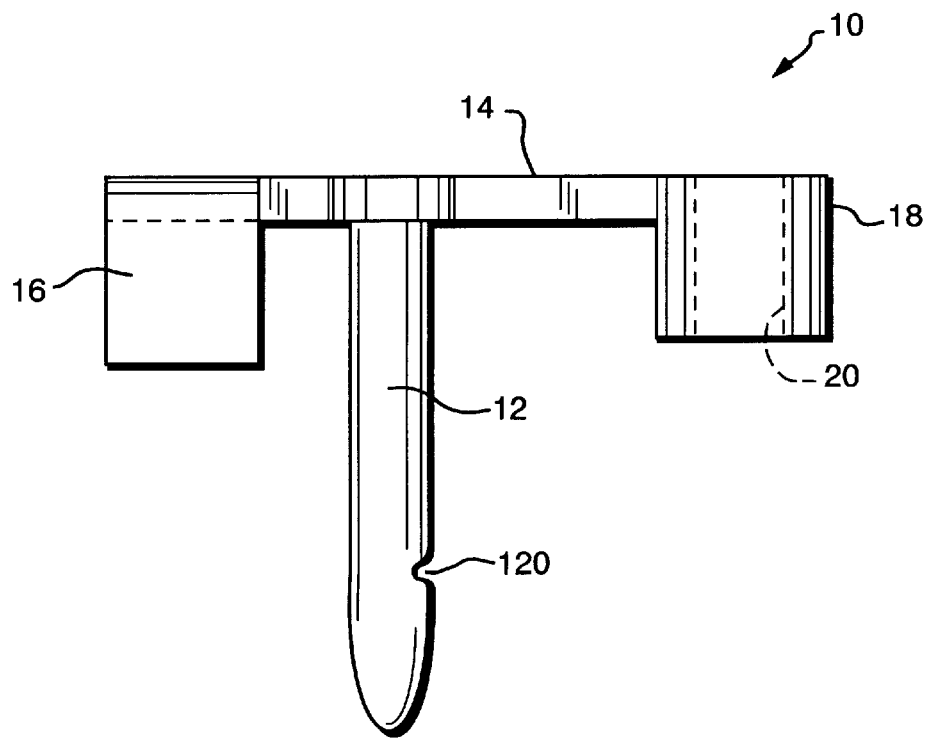
FIG. 2 is a side elevational view thereof.

Referring to FIGS. 1 and 2, the dental implant hole guide extension 10 of the present invention comprises a positioning pin 12 for engaging in the guide recess or hole of a dental guide arrangement disclosed in U.S. Pat. No. 5,888,065 and to be discussed further later in this disclosure.

An arm 14 is connected to the top of pin 12. A generally U-shaped fork 16 at one end of arm 14 has a pair of spaced legs that engage opposite sides of the guide member of the guide arrangement to fix extension 10 in place on the patients jaw. As will be explained later, the guide member has a first guide for use in guiding a drill or bur for creating an initial implant hole. A second guide 18 is connected to the opposite end of arm 14. The second guide 18 has a recess or hole 20 which automatically aligns over the site of the subsequent implant hole and is used to guide the drill for making the subsequent hole in the same way that the first guide was used to make the initial hole.

Figure 3:
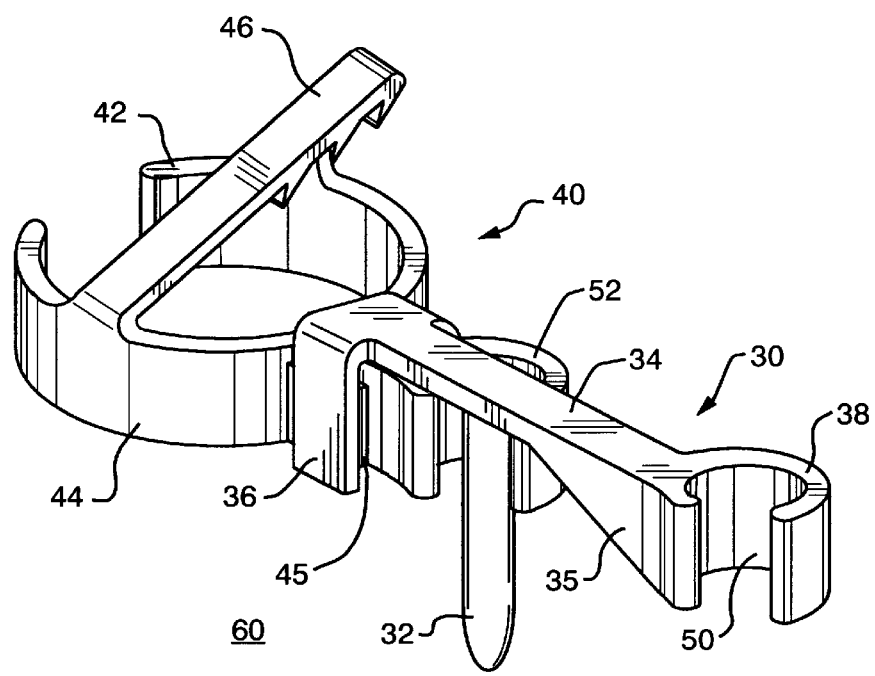
FIG. 3 is a perspective view of another embodiment of the guide extension of the invention, engaged to a guide arrangement of U.S. Pat. No. 5,888,065.

FIG. 3 illustrates another embodiment of the extension 30, engaged to a guide arrangement 40. Arrangement 40 comprises clamp means in the form of a lingual jaw 42 and a buccal jaw 44 which are both arcuate and have an inner concave surface for embracing the respective lingual and buccal surfaces of an appropriate candidate tooth in a patient's jaw bone 60. Jaw attachment means 45 are provided at the mesial end of each generally C-shaped jaw 42 and 44, which fix the relative position of the jaws at this end of the arrangement.

The opposite ends of the jaws are maintained at a spacing from each other even when the jaws are fixed on the tooth, for example, by a toothed rack 46 or using a screw of other means disclosed in U.S. Pat. No. 5,888,065. In this way, means are provided for fixing the arrangement 40 to the tooth.

A guide member 52 is connected to, and extends mesially from the tooth engaging means in the form of jaws 42,44 over the first implant site that has already received the initial hole, and in which positioning pin 32 is provided. Pin 32 is held both by the initial hole and by the first guide in the form of a C-shaped recess at the end of guide member 52. Fork 36 engaged the base of guide member 52 and thus creates a three-point contact with the arrangement 40. This fixes the far end of arm 34 that carries the second guide 38 with its C-shaped or open recess 50. The length of arm 34 is selected to accurately position the recess 50 over the site of the subsequent implant hole to be drilled by a bur that is guided by the second guide 38.

In the embodiment of FIG. 3, arm 34 has an extra support or buttress 35 for helping to keep guide recess perpendicular to the jaw surface despite the thin arm cross-section.

Figure 4:
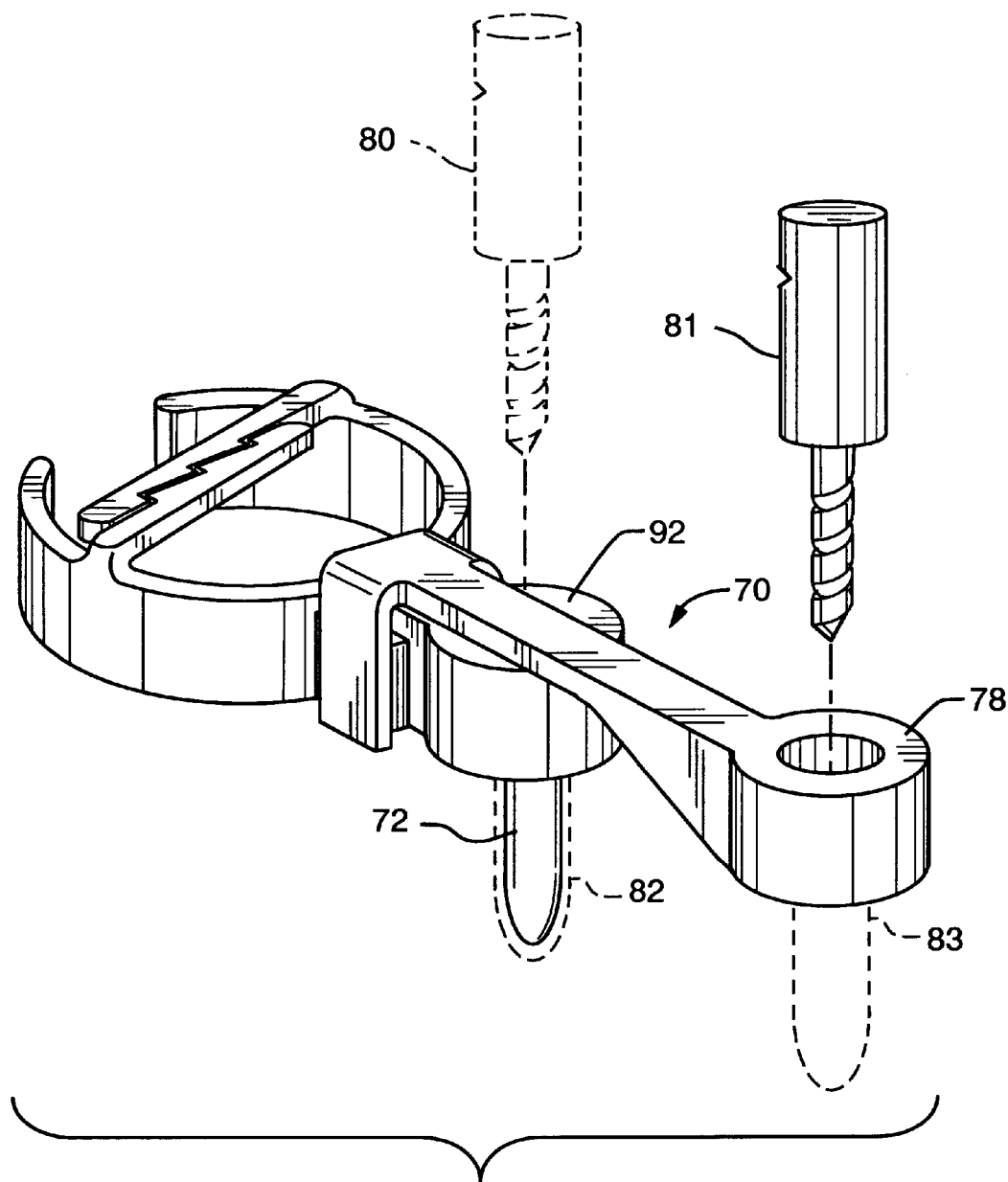
FIG. 4 is a view similar to FIG. 3 of a further embodiment of the invention, also showing the positions of dental drills or burs for making an initial and a subsequent implant hole according the present invention.

FIG. 4 illustrates another embodiment of the invention where the extension 70 has a closed circle as a second guide 78. The second guide may be a recess which extends from 180 to 330° around a circle or from 150 to 360° in the case of a very open to a completely closed recess.

First bur position 80 would be used to make the initial hole 82 in the jaw bone. Pin 72 may extend only in the first guide 92 or, preferably is long enough to extend into hole 82. The recess of second guide 78 is used to guide the bur in its position 81 for drilling the subsequent hole 83.

Throughout the drawings, the same reference numerals are utilized to designate the same or functionally similar parts.

Figure 5:
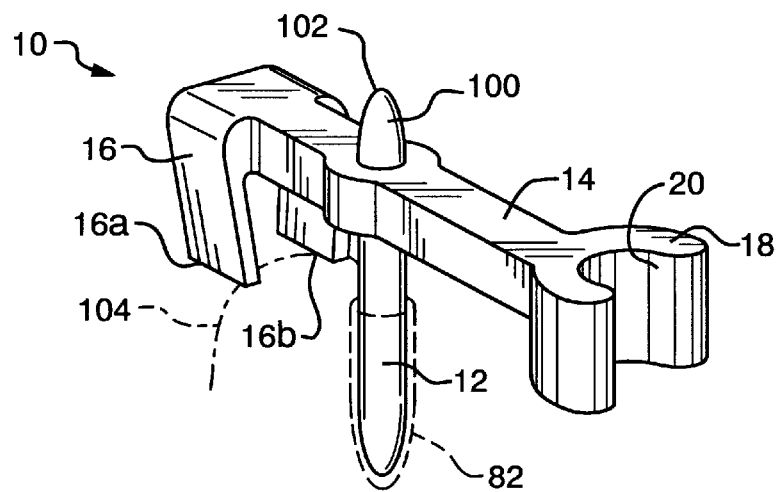
FIG. 5 is a view similar to FIG. 1 showing another embodiment of the invention.

FIG. 5 shows another embodiment of the invention which includes an upwardly extending triangular or pyramid shaped projection 100 which extends vertically upwardly from arm 14 and extends upwardly and centrally, axially with respect to the pin or post 12. The upwardly extending projection 100 has several functions. It is selected to have a vertical height which brings its peak 102, to approximate the height of the natural tooth which has been lost. Peak 102 can thus be used to point to the central developmental groove of the opposing tooth when the patient closes his or her jaw. This gives the practitioner a better guide for the accuracy, location and sufficiency of depth of the initial hole 82 into which pin 12 extends.

Projection 100 also facilitates placement of the device in that it can be held by a dental tool or the fingers of the practitioner. It also gives a parallel reference guide for the second site to be drilled using second guide 18.

FIG. 5 also illustrates how extension device 10 can be used without the guide arrangement that was needed for forming the initial implant hole. The lower ends of the legs of fork 16 form a two-point contact at 16a and 16b to the jaw bone crest whose arch is shown at 104 in phantom line. The initial implant hole 82 extends from the top of that crest downwardly, into the jawbone. With pin 12 in initial hole 82, and the legs of fork 16 touching spaced locations on the crest 104, a three-point contact is achieved that securely holds the extension 10 to the patient's jaw for use as a guide and as a measure of the accuracy, size and position of the initial implant hole 82.

Figure 6:
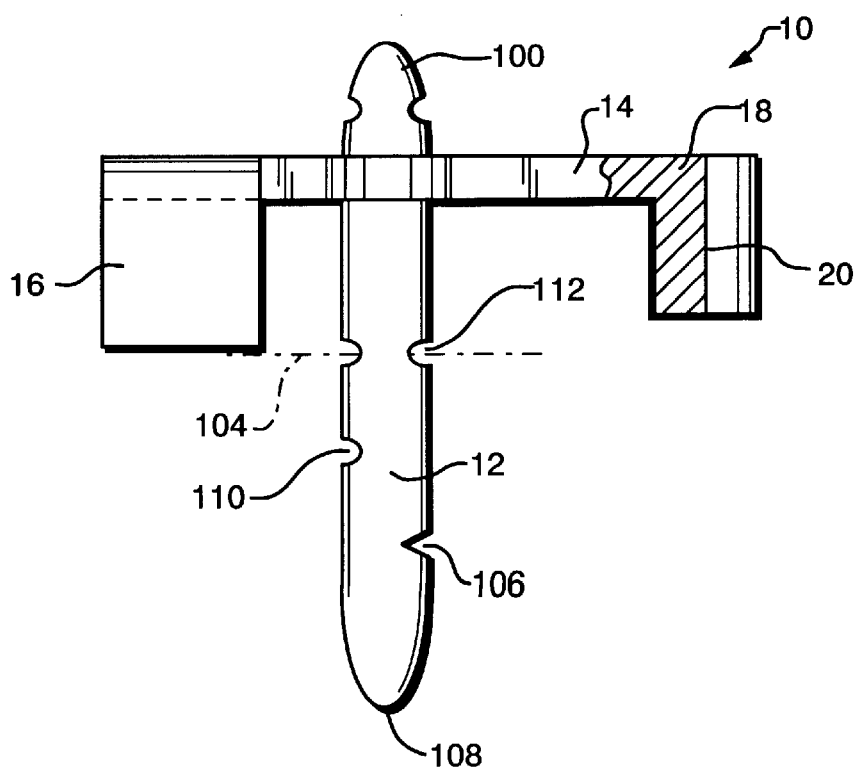
FIG. 6 is a view similar to FIG. 2 showing another embodiment of the invention.

FIG. 6 illustrates another embodiment of the invention where upwardly extending projection 100 has a rounded top. In the embodiments of FIGS. 5 and 6, projection 100 may be triangular, pyramid shaped or any other appropriate shape for achieving the function of a holding mechanism and a measuring and positioning mechanism. In both the embodiments of FIGS. 5 and 6 and also of FIGS. 7 and 8, the projection 100 extends apically in the vertical direction.

Projection 100 in FIG. 6 has the same functions as projection 100 in FIG. 5, including being approximately as high as the natural tooth that would have been above implant hole 82, with a peak for engaging the central groove of the opposing tooth with the jaw closed, to help facilitate placement of the device, and to verify a parallel reference guide for the second drill site.

FIG. 6 also illustrates another feature of pin 12 which is to include vertically spaced markings that can be seen by an X-Ray for gauging the depth of the initial implant hole. In the embodiment of FIG. 6, notches are used as the markings. Pin 12 is selected to have a length of about 9 mm below the bone crest 104 with one mesial notch 106 placed 3 mm up from the lowest point 108 of pin 12. A second distal notch 110 is provided 3 mm up from notch 106. An additional pair of notches 112 (one mesial and one distal) are provided 3 mm up from notch 110. If the initial implant hole 82 is insufficiently deep, the top notch pair 112 will be viewed in the X-Ray as being above the crest 104 by an amount that can be gauged for use in helping the dental practitioner further drill the initial hole to the proper depth.

Additional notches are provided in the upwardly extending projection 100 so that the guide extension 10 can be grasped by a tool more easily.

Figure 7:
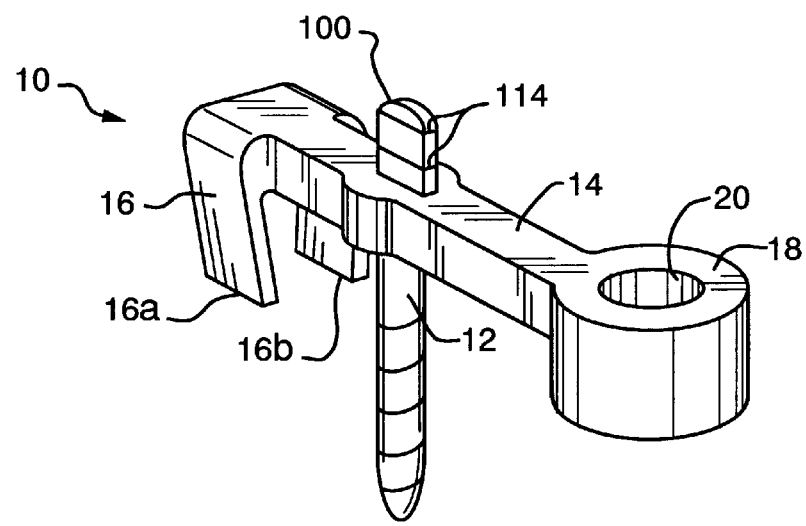
FIG. 7 is a view similar to FIG. 1 showing a still further embodiment of the invention.

FIG. 7 illustrates a still further embodiment of the invention which utilizes a flat substantially rectangular projection 100 with spaced grooves 114, spaced 2 mm apart. Advantageously, each notch in the embodiment of FIG. 6 and each groove in the embodiment of FIG. 7 is approximately 0.25 mm in height and depth.

Below arm 14 and starting at the bone crest which approximately corresponds to the bottom ends 16a and 16b of fork 16, pin 12 extends 10 mm and has 2 mm markings. Although pin 12 is shown to be cylindrical, in an alternate embodiment of the invention it can be a flat blade shape similar to the shape of upwardly extending projection 100. Again, 3-point contact is achieved between the initial hole and the bone crest or the guide arrangement for drilling the initial implant hole. Markings 114 on the vertical projection 100 are provided both to help grip the device and to gauge crown height for the prosthetic tooth to be used over the implant fixture to be installed later.

Figure 8:
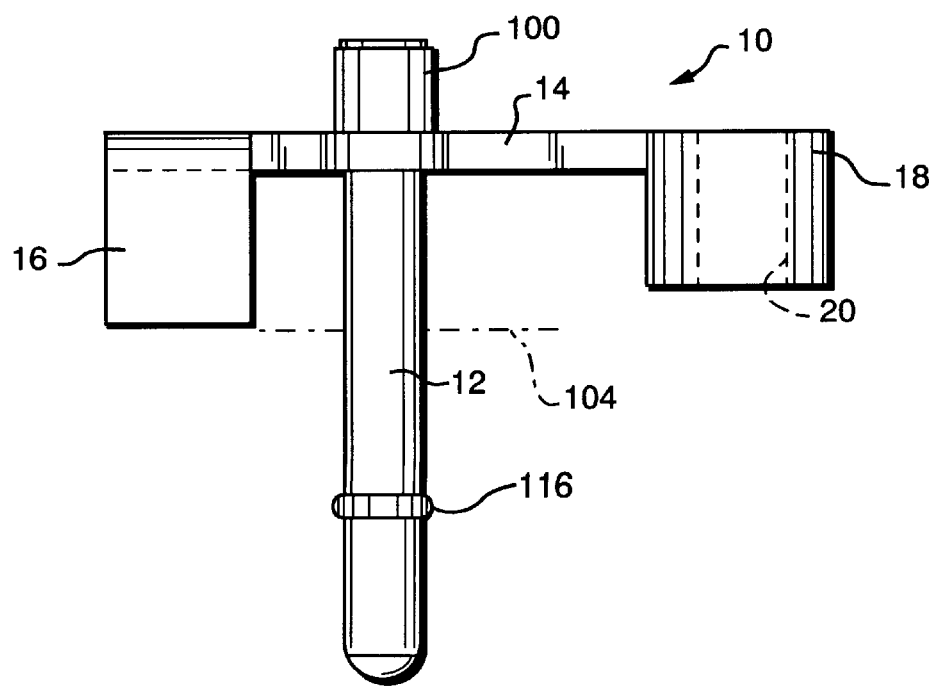
FIG. 8 is a view similar to FIG. 2 showing a still further embodiment of the invention.

FIG. 8 illustrates a still further embodiment of the invention where vertical projection 100 is a cylindrical knurled handle for the device 10. In addition to the advantages that are shared by the projections 100 in the embodiments of FIGS. 5, 6 and 7, the embodiment of FIG. 8 includes a circumferential bump or convex projection 116 on the outer surface of pin 12, approximately half way down from the crest position 104. Pin 12 is assumed to have a depth in the initial implant hole of 10 mm with radial projection 116 being spaced about 5 mm from the lower end of the pin and about 5 mm from the crest position 104. Convex projection 116 serves to engage the inner surface of the initial hole and advantageously has a thickness beyond the surface of pin 12 of 0.25 mm. In this way, with pin 12 having a diameter of 2.5 mm, the diameter of projection 116 is 3.0 mm, corresponding to the diameter of a typical implant hole. Projection or ring 116 helps further lock the device 10 in place and further enhances the 3-point anchoring of the device. It also provides a landmark for an X-Ray image.

Returning to FIG. 2, a single rudimentary notch 120 is illustrated about halfway down the portion of pin 12 which is meant for engagement into the initial implant hole.

In all the embodiments of the invention, pin 12 can include vertically spaced markings that act as gauges that are visible to X-Rays, with the markings being any one of a radial projection, a notch or a groove. The markings are advantageously 2 mm or 3 mm apart but can be from 1 mm to 5 mm apart.

The vertical projection 100 is advantageously 6 mm tall with markings every 2 mm. The upwardly extending projection is dictated by the height of the tooth to be provided at the implant site 82 however, and should be selected accordingly.

FIG. 5 also illustrates how second guide 18 may be semi-circular or another portion of a circle which is open in the mesial direction rather than in the buccal direction as in the embodiment of FIG. 3.

While specific embodiments of the invention have been shown and described in detail to illustrate the application of the principles of the invention, it will be understood that the invention may be embodied otherwise without departing from such principles.

What is claimed is:

1. A dental implant hole guide extension for drilling a subsequent implant hole and for use with an arrangement for drilling an initial implant hole, the arrangement having tooth engagement means for engaging a tooth which is adjacent a site in a patient's mouth for receiving the initial hole, fixing means connected to the engagement means for fixing the engagement means to the tooth and a guide member connected to the tooth engagement means and adapted to extend over the initial hole, the guide member having a first guide aligned with the initial hole, the extension comprising:

a positioning pin for engagement in the initial hole;

an arm connected to the pin for extending over the initial hole and toward a site of the subsequent hole;

guide member engaging means connected to the arm on one side of the pin for firmly engaging the guide member to hole; the arm to the guide member; and a second guide connected to the arm on an opposite side of the pin for guiding a dental bur for drilling the subsequent implant hole.

2. An extension according to claim 1, wherein guide engaging means comprises a fork having a pair of legs for engaging the guide member.

3. An extension according to claim 2, wherein the pin is long enough to also extend into the initial hole.

4. An extension according to claim 3, including a support connected between the arm and the second guide.

5. An extension according to claim 1, wherein the second guide comprises a recess.

6. An extension according to claim 5, wherein the recess extends around a circle by about 150 to 360°.

7. An extension according to claim 6, wherein the recess extends around a portion of a circle by about 180° to 330°.

8. An extension according to claim 1, wherein the entire extension is sterilizable.

9. An extension arrangement according to claim 1, wherein the second guide is a closed circle.

10. An extension according to claim 1, including a vertically extending apical projection on the arm, centered with and parallel to the pin.

11. An extension according to claim 10, including at least one marking on the apical projection.

12. An extension according to claim 10, wherein the apical projection is knurled.

13. An extension according to claim 1, wherein the pin includes at least one marking along its length at a location below a bone crest of a jaw bone containing the initial implant hole when the pin is in the initial hole.

14. A dental implant hole guide extension for drilling a subsequent implant hole after an initial implant hole has been drilled at an initial site in a patient's jaw bone, the extension comprising:

a positioning pin for engagement in the initial hole;

an arm connected to the pin for extending over the initial hole and toward a site of the subsequent hole;

a fork having a pair of legs connected to the arm on one side of the pin for engaging a bone crest of the jaw bone at two points to hold the arm in a guide position; and a second guide connected to the arm on an opposite sides of the pin for guiding a dental bur for drilling the subsequent implant hole.

15. An extension according to claim 14, wherein the pin is long enough to also extend into the initial hole.

16. An extension according to claim 14, including a support connected between the arm and the second guide.

17. An extension according to claim 14, wherein the second guide comprises a recess.

18. An extension according to claim 14, wherein the second guide is a closed circle.

19. An extension according to claim 14, including a vertically extending apical projection on the arm, centered with and parallel to the pin.

20. An extension according to claim 19, including at least one marking on the apical projection.

21. An extension according to claim 19, wherein the apical projection is knurled.

22. An extension according to claim 14, wherein the pin includes at least one marking along its length at a location below a bone crest of a jaw bone containing the initial implant hole when the pin is in the initial hole.

23. An extension according to claim 22, wherein the marking is one of a notch, a groove and a radial projection.

24. An extension according to claim 22, including a plurality of said markings which are vertically spaced on the pin at spacings of from 1 to 5 mm.

* * * * *